United States Patent
Quinlin et al.

(10) Patent No.: US 6,844,473 B1
(45) Date of Patent: Jan. 18, 2005

(54) CONTINUOUS ASPIRATION PROCESS FOR MANUFACTURE OF ULTRA-FINE PARTICLE HNS

(75) Inventors: William T. Quinlin, Amarillo, TX (US); Raymond Thorpe, Amarillo, TX (US); Maury L. Sproul, Amarillo, TX (US); Dillard M. Cates, Amarillo, TX (US)

(73) Assignee: BWXT Pantex, L.L.C., Amarillo, TX (US)

( * ) Notice: Subject to any disclaimer, the term of this patent is extended or adjusted under 35 U.S.C. 154(b) by 0 days.

(21) Appl. No.: 10/783,533

(22) Filed: Feb. 18, 2004

(51) Int. Cl.[7] ............................................. C07C 205/00
(52) U.S. Cl. ..................................................... 568/931
(58) Field of Search .......................................... 568/931

(56) References Cited

FOREIGN PATENT DOCUMENTS

EP     0277386 A2  *  12/1987

* cited by examiner

*Primary Examiner*—J. Parsa
(74) *Attorney, Agent, or Firm*—D. Neil LaHaye

(57) ABSTRACT

A process for the manufacture of ultra-fine-particle hexanitrostilbene (HNS). Hexanitrostilbene is mixed in n-methylpyrrolidone (NMP) and the solution is steam heated for approximately one hour. The solution is rapidly mixed with cold water by means of drawing it through an aspirator through which water is flowing. The produced slurry is captured in a receiver and then filtered through a 0.45-micron filter. The recovered HNS product is then freeze dried.

6 Claims, No Drawings

CONTINUOUS ASPIRATION PROCESS FOR MANUFACTURE OF ULTRA-FINE PARTICLE HNS

BACKGROUND OF THE INVENTION

1. Field of the Invention

The invention is generally related to organic nitroaromatics, and more specifically to a process for the manufacture of ultra-fine-particle hexanitrostilbene.

2. General Background

Hexanitrostilbene, an organic nitroaromatic abbreviated as HNS and also called hexanitrodiphenylethylene, is a heat resistant explosive that is commonly used in deep well charges found in the oil field or in applications requiring the explosive to withstand significant temperatures before initiation. The chemical formula is $C_{14}H_6N_6O_{12}$. HNS is made in type I and type II and grades A and B. The difference between type I and type II is primarily the particle size. The particle size of type I is 1–5 microns. The particle size of type II is 100–300 microns. HNS has a uniquely small critical diameter of 0.020 inch. It is relatively insensitive to heat, spark, impact, and function, yet it finds wide use as a heat resistant booster charge for military applications.

Certain uses, or proposed uses, of HNS require high purity HNS with a surface area greater than 10 square meters per gram but containing little residual solvent. The ability to manufacture HNS that meets these requirements in a continuous or batch process at suitable economic and efficiency levels is not addressed in the known art.

SUMMARY OF THE INVENTION

The invention addresses the above needs. What is provided is a process for the manufacture of ultra-fine-particle hexanitrostilbene (HNS). Hexanitrostilbene is mixed in n-methylpyrrolidone (NMP) and the solution is steam heated for approximately one hour. The solution is rapidly mixed with cold water by means of drawing it through an aspirator through which water is flowing. The produced slurry is captured in a receiver and then filtered through a 0.45 micron filter. The recovered HNS product is then freeze dried.

DETAILED DESCRIPTION OF THE PREFERRED EMBODIMENT

The invention is directed to a process for the manufacture of ultra-fine-particle hexanitrostilbene (HNS) that is especially useful in detonators.

Several manufacturing concepts were considered and tested to determine which would meet the requirements for the use of HNS in laser slapper detonators.

In a concept for a batch process, 1.2 grams of HNS-II is dissolved in 800 ml boiling acetonitrile ($CH_3CN$). The HNS is crash precipitated by quickly transferring the hot solution into 800 ml of chilled water (10 degrees Celsius) while stirring vigorously. The resulting mixture is filtered through a 0.45-micron filter to recover the HNS product and the HNS product is then freeze dried. This concept produces a surface are of 7–10 square meters per gram with a purity of greater than 99%. The amount of solvent in the product is approximately 0.10%. This concept produces approximately 1350 ml of waste per gram of product.

In a second concept, a solution of 1.2 grams of HNS in 800 ml of boiling acetonitrile ($CH_3CN$) is pushed by an inert gas such as nitrogen into chilled water in a vessel with an overflow spout. The chilled water is fed into the bottom of the overflow vessel by a peristalic pump. As the chilled water mixes with the solution of HNS, the overflow is pulled by vacuum and gravity into a vacuum receiver. The resulting slurry is filtered through a 0.45-micron filter and the recovered HNS is freeze dried. This concept produces a surface area of 4–5 square meters per gram of HNS with a purity of greater than 99%. This concept produces anywhere from 2500 to 4200 ml of waste per gram of product. Sensitivity testing to obtain threshold values and solvent content has not been determined for HNS precipitated by this process due to the fact that the low surface area is not suitable for the intended use.

In a third concept, a solution of 1.2 grams of HNS in 800 ml of acetonitrile ($CH_3CN$) heated to 82 degrees Celsius is drawn through a polypropylene aspirator valve with tap water flowing through at approximately four liters per minute. The aspiration process is completed in less than one minute. The produced slurry is captured in a receiver and then filtered through a 0.45-micron filter. The recovered HNS product is freeze dried. This concept produces an average surface area of approximately 20 square meters per gram of HNS with a purity of greater than 98%. This process produces approximately 4200 ml of waste per gram of product. The amount of solvent in the produced HNS has not been determined.

A fourth concept uses the continuous aspiration process described above with a different solvent. A solution of 15 grams of HNS in 400 ml n-methylpyrrolidone (NMP) is steam heated to a temperature of 82 degrees Celsius for approximately one hour and then drawn through a polypropylene aspirator valve with tap water flowing at approximately four liters per minute. The aspiration process is completed in less than one minute. The produced slurry is captured in a receiver and then filtered through a 0.45-micron filter. The recovered HNS product is freeze dried. This concept produces a surface area of 38–43 square meters per gram of HNS with a purity of greater than 98%. The solvent content is less than 0.01%. This concept produces approximately 180 ml of waste per gram of product.

In testing the product of the various concepts, the solvent content was determined by gas chromatography and purity was determined by high pressure liquid chromatography.

Each of the unique processes described above has advantages and disadvantages. The selection of which process to use for manufacturing fine-particle or ultra-fine-particle HNS will depend upon the surface area requirements of the produced HNS as well as the costs and time involved. For the use of HNS particles in laser slapper detonators, the process of continuous aspiration described above using NMP as a solvent is the preferred process due to the high surface area of the product and the low waste volume.

Because many varying and differing embodiments may be made within the scope of the inventive concept herein taught and because many modifications may be made in the embodiment herein detailed in accordance with the descriptive requirement of the law, it is to be understood that the details herein are to be interpreted as illustrative and not in a limiting sense.

What is claimed as invention is:

1. A process for the manufacture of ultra-fine-particle hexanitrostilbene, comprising the steps:

a. mixing hexanitrostilbene with n-methylpyrrolidone at a ratio of 15 grams hexanitrostilbene per 400 ml n-methylpyrrolidone;

b. heating the mixture to a temperature of 82 degrees Celsius;

c. mixing the heated solution with cold water by aspiration;

d. capturing the resulting slurry in a receiver;

e. filtering the slurry; and f. drying the filtered slurry.

2. The process of claim 1, wherein the step of heating the mixture is held for a time period of approximately one hour.

3. The process of claim 1, wherein the step of mixing the heated solution with cold water is accomplished by drawing it through an aspirator through which water is flowing.

4. The process of claim 1, wherein the step of filtering the slurry uses a 0.45-micron filter.

5. The process of claim 1, wherein the step of drying the filtered slurry is accomplished using freeze drying.

6. A process for the manufacture of ultra-fine-particle hexanitrostilbene, comprising the steps:

a. mixing hexanitrostilbene with n-methylpyrralidone at a ratio of 15 grams hexanitrostilbene per 400 ml n-methylpyrralidone;

b. steam heating the mixture to a temperature of 82 degrees Celsius for a time period of approximately one hour;

c. mixing the heated solution with cold water by drawing it through an aspirator through which water is flowing;

d. capturing the resulting slurry in a receiver;

e. filtering the slurry using a 0.45-micron filter; and f. freeze drying the filtered slurry.

\* \* \* \* \*